United States Patent [19]
Singh et al.

[11] Patent Number: 6,087,383
[45] Date of Patent: Jul. 11, 2000

[54] BISULFATE SALT OF HIV PROTEASE INHIBITOR

[75] Inventors: Janak Singh, Lawrenceville; Madhusudhan Pudipeddi, Plainsboro; Mark D. Lindrud, Basking Ridge, all of N.J.

[73] Assignee: Bristol-Myers Squibb Company, Princeton, N.J.

[21] Appl. No.: 09/217,538

[22] Filed: Dec. 21, 1998

Related U.S. Application Data

[60] Provisional application No. 60/071,968, Jan. 20, 1998.
[51] Int. Cl.$^7$ .......................... A61K 31/44; C07D 213/56
[52] U.S. Cl. ................................ 514/357; 546/332
[58] Field of Search .............................. 546/332; 514/357

[56] References Cited

U.S. PATENT DOCUMENTS 5,849,911 12/1999 Fassler et al. ........................ 544/335

FOREIGN PATENT DOCUMENTS

WO97/40029 10/1997 WIPO .

Primary Examiner—Bernard Dentz
Attorney, Agent, or Firm—David M. Morse

[57] ABSTRACT

The present invention provides the crystalline bisulfate salt of the formula

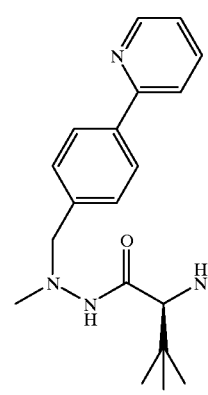

which is found to have unexpectedly high solubility/dissolution rate and oral bioavailability relative to the free base form of this azapeptide HIV protease inhibitor compound.

2 Claims, 5 Drawing Sheets

BISULFATE SALT OF HIV PROTEASE INHIBITOR

This application claims priority from Provisional Application 60/071,968 filed Jan. 20, 1998.

BACKGROUND OF THE INVENTION

1. Field of the Invention

The present invention provides the novel crystalline bisulfate salt of the azapeptide HIV protease inhibitor of the formula

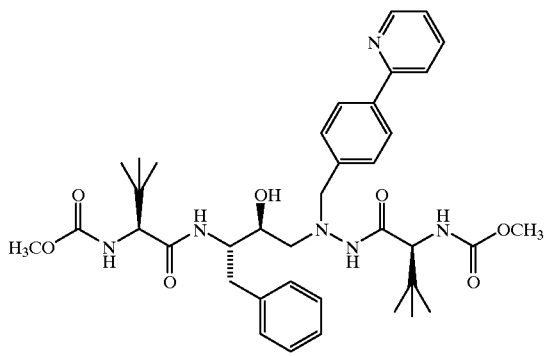

which exhibits unexpectedly superior aqueous solubility/dissolution behavior compared to other salts, and significantly improved oral bioavailability in animals compared to the free base. The bisulfate salt is thus useful for pharmaceutical dosage forms of the above-indicated protease inhibitor, particularly oral dosage forms.

2. Background Art

Published PCT patent application WO 97/40029 discloses a series of azapeptide HIV protease inhibitors reported to have a high degree of inhibitory activity against the HIV virus. One of the agents included within the scope of WO 97/40029 is the compound having the structural formula

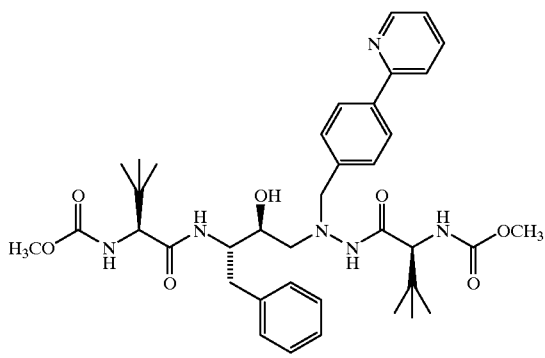

and the chemical name [3S-(3R*, 8'R*, 9'R*, 12R*)]-3,12-bis(1,1-dimethylethyl)-8-hydroxy-4,11-dioxo-9-(phenylmethyl)-6-[[4-(2-pyridinyl)phenylmethyl]-2,5,6,10,13-pentaazatetradecanedioic] acid, dimethyl ester and is under evaluation as a possible second generation HIV protease inhibitor.

WO 97/40029 discloses the free base form of azapeptide derivatives such as compound I and also various pharmaceutically acceptable acid addition salts. While several organic and inorganic acids are mentioned as possible salt-forming agents, including sulfuric acid, there is no mention of the particular bisulfate salt which is the subject of the present application.

SUMMARY OF THE INVENTION

The present invention provides the bisulfate salt of compound I above having the structural formula

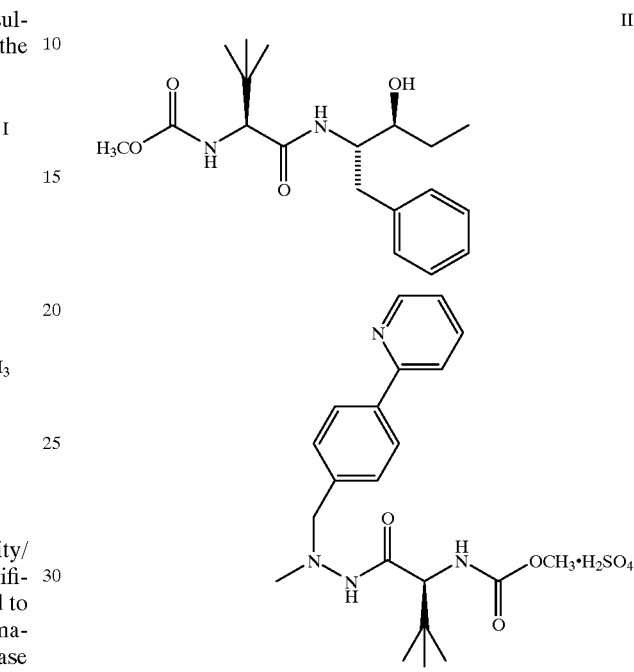

DETAILED DESCRIPTION OF THE INVENTION

Compound I as disclosed above is a weak organic base with an aqueous solubility of less than 1 μg/mL at 24±3° C. The crystalline free base form as a suspension in water or oil has poor oral bioavailability in animals, probably because of its extremely low solubility in these vehicles.

For development of pharmaceutical formulations, particularly oral dosage forms, the active ingredient must have sufficient oral bioavailability. Since the free base form of compound I did not possess such bioavailability, acid addition salts were explored by the present inventors. A number of commonly used acid addition salts such as the hydrochloride, benzenesulfonate, methanesulfonate, p-toluenesulfonate, phosphate, nitrate, 1,2-ethanedisulfonate, isethionate and sulfate were evaluated, in addition to the bisulfate salt of the present invention. All of these salts in their crystalline form exhibited lower aqueous solubility (1–3 mg/mL or less at 24±3° C.) than the bisulfate which had a solubility under the same conditions of approximately 4–5 mg/mL.

Solid state transformation was observed when the other acid addition salts mentioned above were suspended in water, probably due to their dissociation to form the free base. In the majority of cases, this transformation was accompanied by gel formation. Unlike the other salts mentioned above, the extra proton of the bisulfate salt prevents the conversion to the free base which, as mentioned above, is very insoluble in water and has poor oral bioavailability. The unusual solubility behavior of the bisulfate salt in water is further elaborated in the following.

In general, conversion of salts to the unionized form or vice versa can be explained on the basis of pH-solubility theory. The solubility of the free base in water was determined as a function of pH at 24±3° C. and is shown below. The pH at which the compound exhibits the highest solubility is referred to as $pH_{max}$ and was found to be approximately 1.2. It has been reported in the literature that at $pH>pH_{max}$ of a weakly basic organic compound, the equilibrium solid phase in an aqueous suspension of the compound is the free base. At $pH<pH_{max}$ the equilibrium solid converts to the corresponding salt form. The term "equilibrium solid phase" refers to the undissolved or excess solid in a suspension of the compound in water after sufficient equilibration time. When a salt of a weak base is equilibrated in water in an amount exceeding its solubility limit (i.e., a suspension of the salt in water), the resulting pH of the suspension may fall on either side of the $pH_{max}$ depending on the strength of the acid among other factors. When the resulting pH is greater than the $pH_{max}$, the suspended solid converts to the free base.

Figure 1:
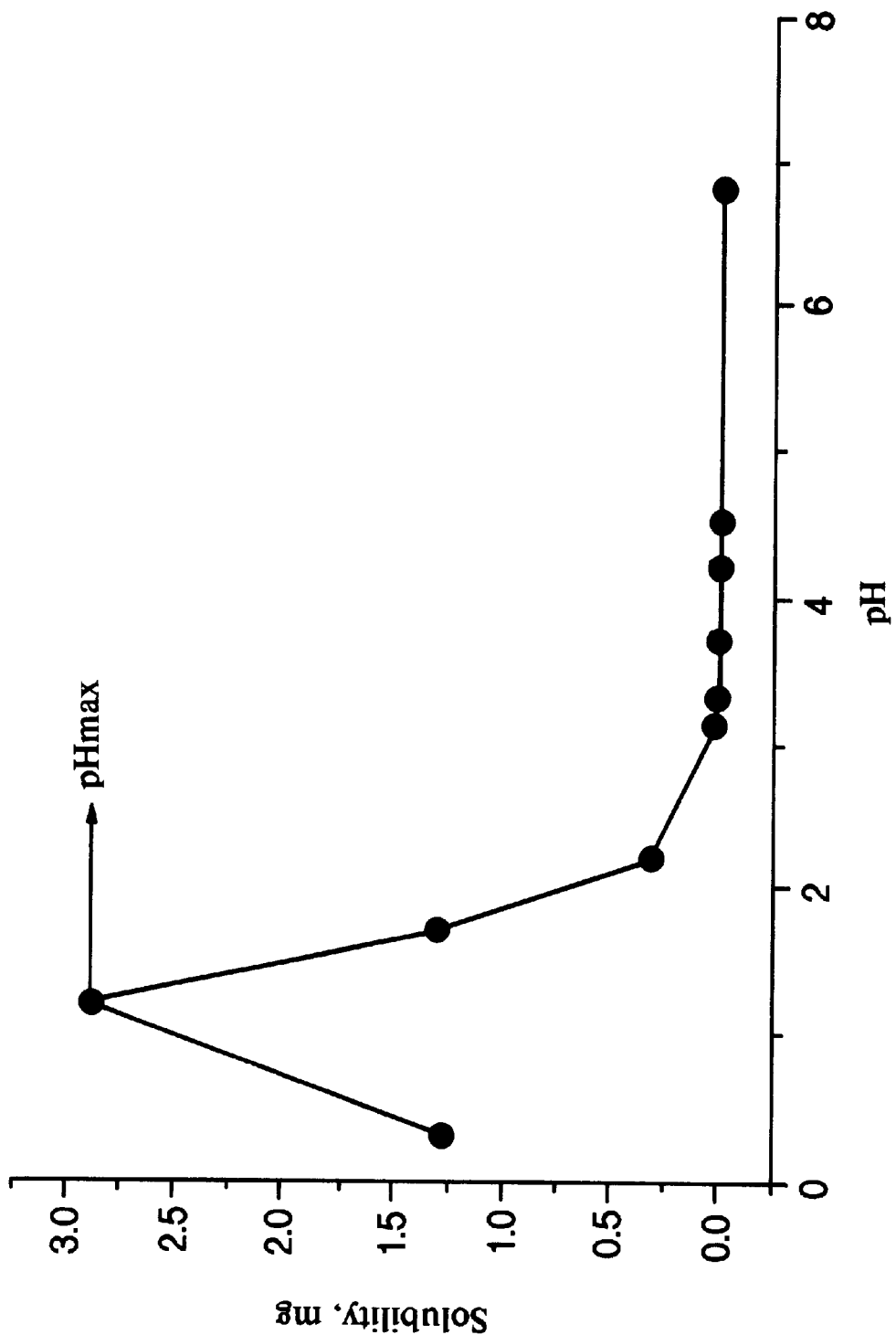

Studies conducted with methane sulfonate and hydrochloride salts, in particular, of the free base confirmed the above described general findings reported in the literature. Amounts in excess of the solubility of these salts were equilibrated in water at 24±3° C. for at least 24 hours. The pH of the suspensions after equilibration was 2.1±0.1 which is greater than the $pH_{max}$. The undissolved solids from these suspensions were isolated, air-dried, and characterized. By thermal and elemental analysis the undissolved solids from these suspensions were identified as the free base. This behavior was expected based on the pH-solubility profile shown in FIG. 1 and the studies reported in the literature.

When an excess amount of the bisulfate salt was equilibrated in water a modification occurred in the solid phase in equilibrium with solution. However, the undissolved solid phase after equilibration was not the free base, although the pH (1.9±0.2) of the suspension was greater than the $pH_{max}$ and comparable to the pH of the suspensions of methane sulfonate and hydrochloride salts described above. The solid phase after at least 24 hours of equilibration was identified by elemental analysis as a hydrated form of 2:1 salt of the free base form and sulfuric acid (referred to as the sulfate salt). This behavior of the bisulfate salt is unexpected based on pH-solubility theory.

When an excess amount of the sulfate salt, in turn, was equilibrated in water a modification occured in the solid phase in equilibrium with solution. The undissolved solid from this suspension was isolated, air-dried, and characterized. Thermal and elemental analysis of this undissolved solid phase was similar to that of the free base although the conversion of the sulfate salt to the free base was not as definitive as that of the methane sulfonate and hydrochloride salts. From a pharmaceutical point of view the propensity of salts to convert to the free base in an aqueous environment is not desirable due to the low oral bioavailability of the free base. Thus, the bisulfate salt due its unique solubility behavior in water offered unexpected superiority.

The solubility behavior of the bisulfate salt in water was also unexpected considering the interaction of compound I free base and sulfuric acid in water. For example, the free base exhibited a solubility of less than 1 mg/mL in water at a pH of ~1.8 adjusted with sulfuric acid, compared to 4–5 mg/mL solubility of the bisulfate salt in water at comparable pH conditions. Based on pH-solubility theory the free base and the salt are expected to exhibit similar solubility at a given pH.

The enhanced solubility/dissolution behavior of the bisulfate contributes to its improved oral bioavailability in animals relative to the free base. The absolute oral bioavailability of the bisulfate salt was found to be approximately 20% in dogs when administered in unformulated solid form placed in a gelatin capsule. In comparison, the crystalline free base had minimal oral bioavailability in dogs.

Figure 2A:
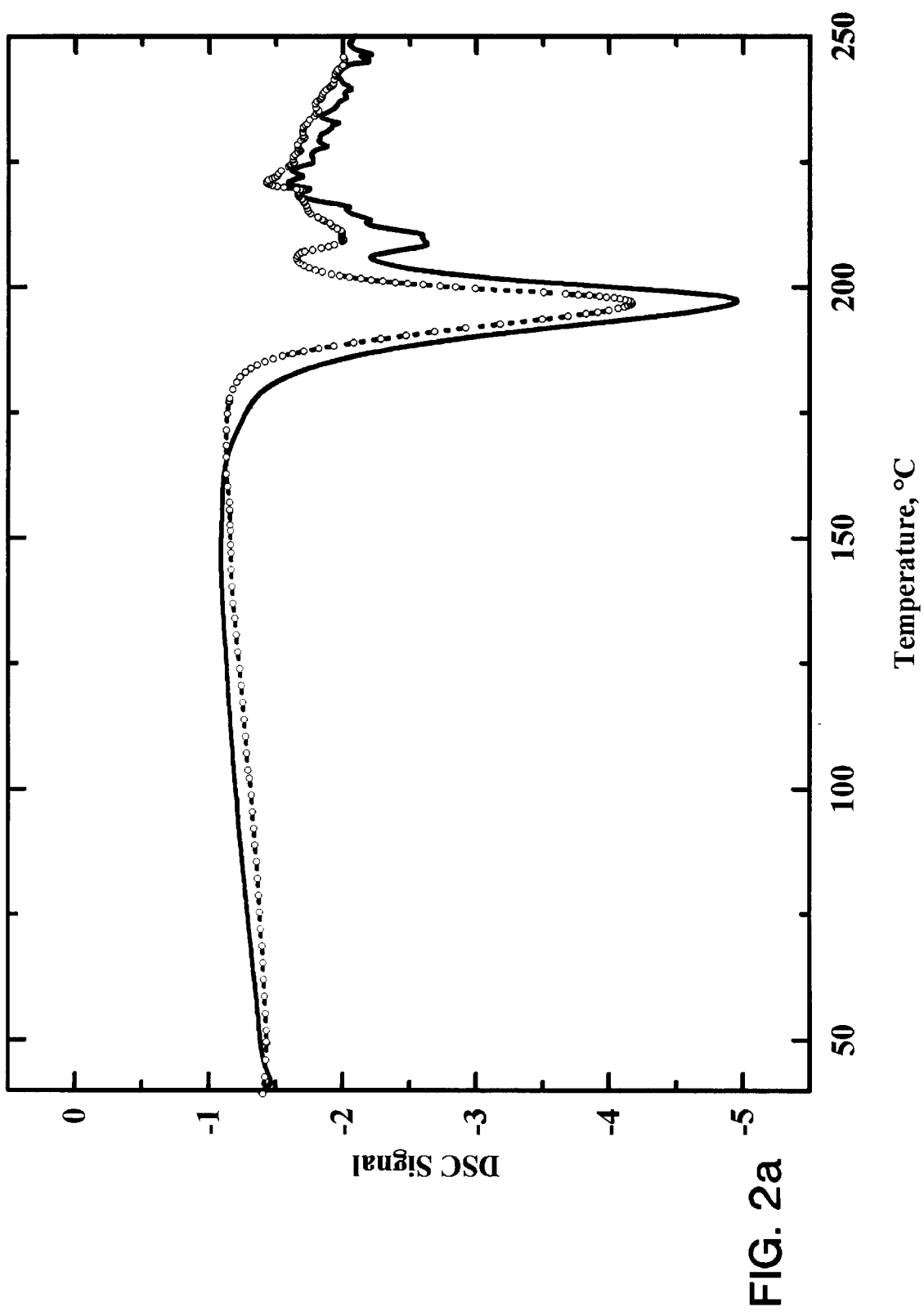
Figure 2B:
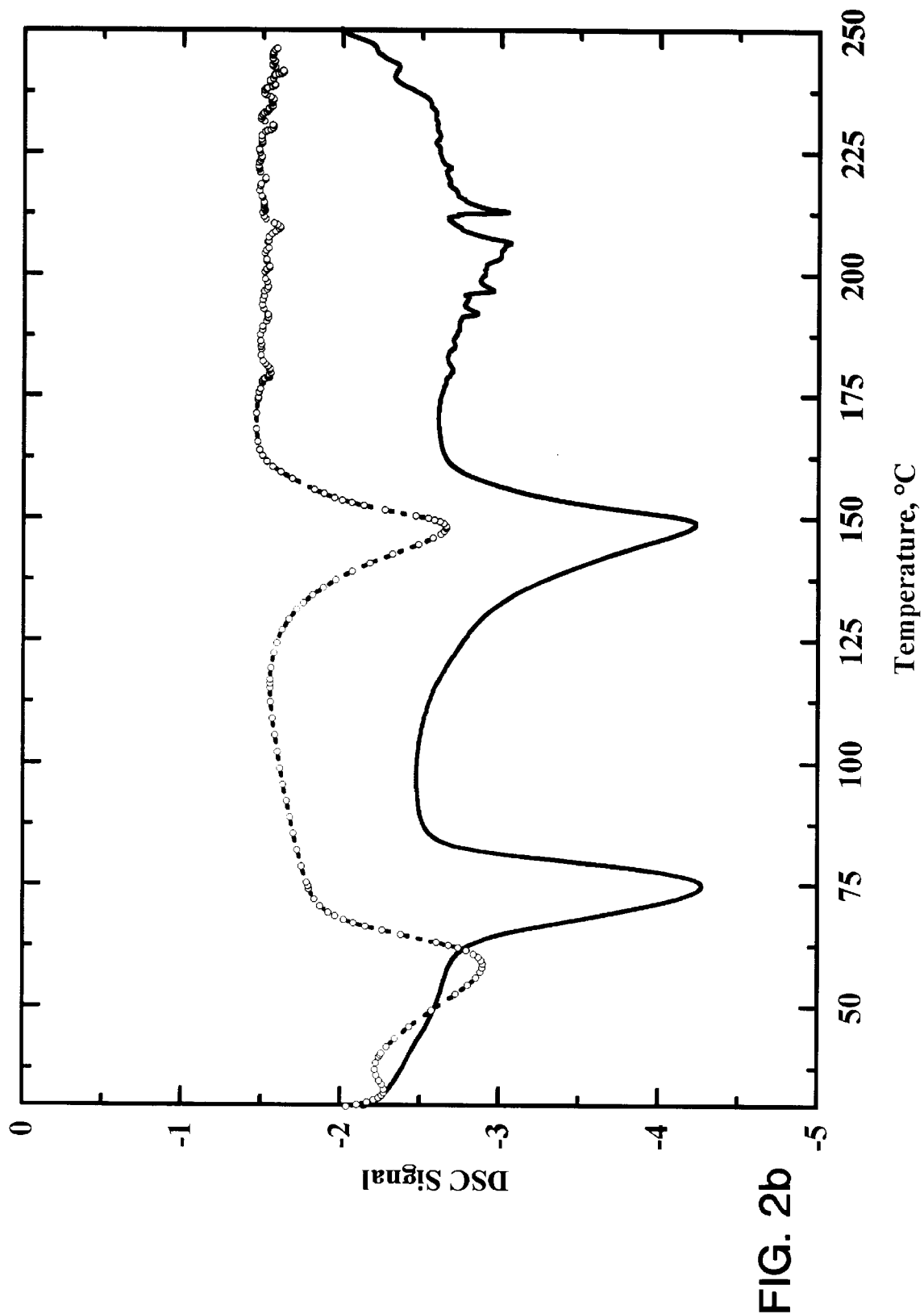

In addition to optimal solubility, satisfactory physical stability in the solid-state is another desirable property of pharmaceutical salt forms. The term physical stability indicates the ability of the salt form to retain its crystal structure (including solvents of crystallization, if any) under storage/stress conditions. Significant changes in the physical nature of the salt form as indicated by thermal methods such as differential scanning calorimetry are undesirable. The bisulfate salt exhibited excellent solid-state physical stability when stored at 40° C./75% relative humidity (RH) for as long as 9 months as shown in FIG. 2a. Differential scanning calorimetry revealed no significant changes in the thermal behavior of the stressed sample of the bisulfate salt compared to that of the unstressed sample (stored at 2–8° C. in a closed container). The methane sulfonate, hydrochloride, and the sulfate salts, on the other hand, showed significant changes in their thermal behavior when stored at 40° C./75% RH for as little as two weeks as shown in FIGS. 2b, c, and d. While differences in physical stability of salt forms is not unusual, the propensity of a particular salt to form solvates (or crystal modifications) and its ability to retain the solvent of crystallization (the physical stability of crystal modifications) under storage/stress conditions cannot be predicted apriori.

FIG. 2a represents Physical stability of the bisulfate salt. The solid line represents the unstressed material. The dotted line represents the material stressed at 40° C./75% RH for 9 months.

FIG. 2b represents Physical Stability of the hydrochloride salt. The solid line represents the unstressed material. The dotted line represents the material stressed at 40° C./75% RH for two weeks.

Figure 2C:
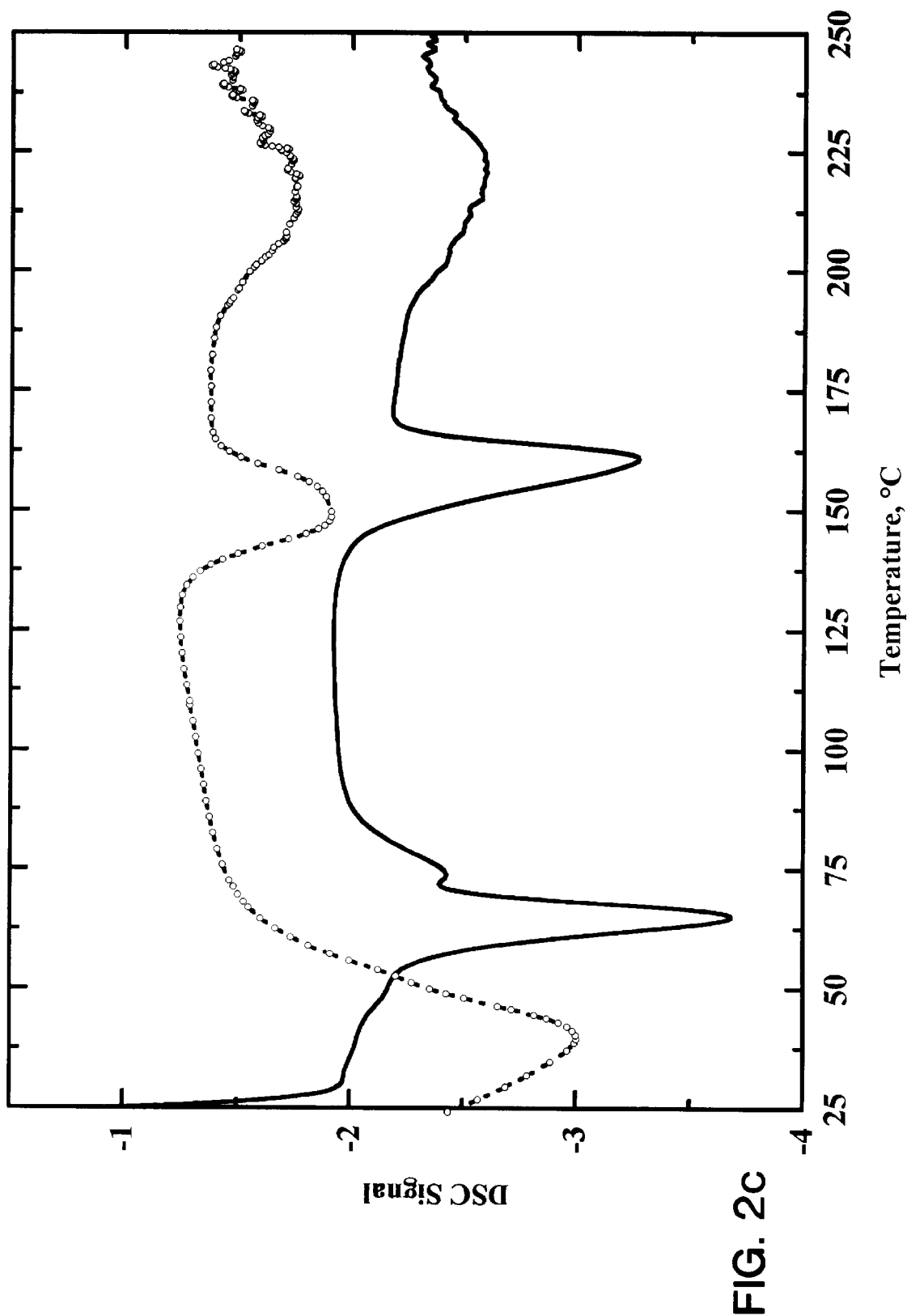
Figure 2D:
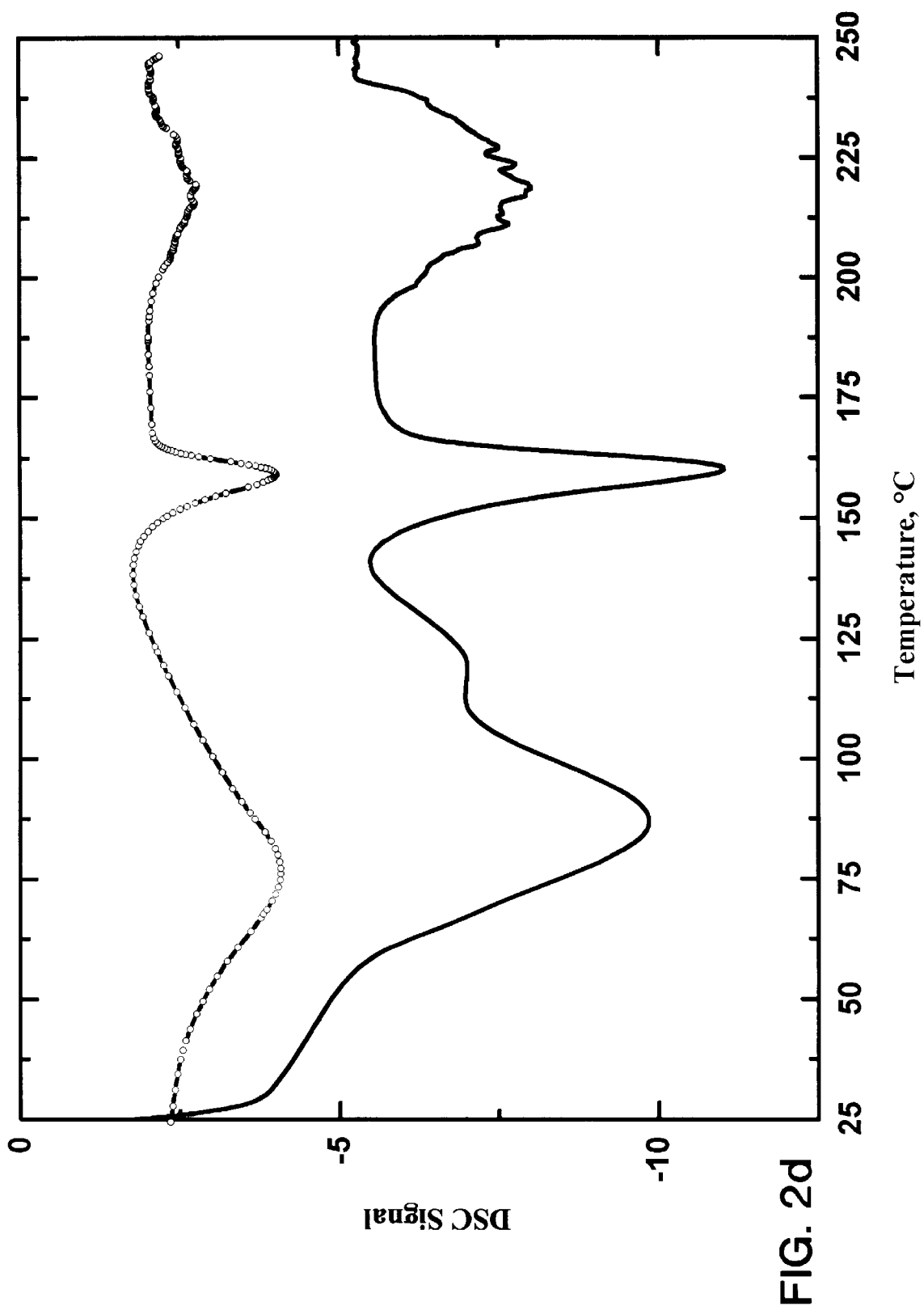

FIG. 2c represents Physical stability of the methane sulfonate salt. The solid line represents the unstressed material. The dotted line represents the material stressed at 40° C./75% RH for two weeks FIG. 2d represents Physical stability of the sulfate salt. The solid line represents the unstressed material. The dotted line represents the material stressed at 40° C./75% RH for two weeks.

The bisulfate salt may be prepared by forming a solution of free base of compound I with sulfuric acid in solvents such as acetonitrile, isopropanol, ethanol, or acetone and then isolating the so-produced bisulfate salt.

Because of its high bioavailability as well as its good crystallinity and stability, the bisulfate salt is very useful in preparing oral dosage forms of compound I. The examples which follow illustrate preparation of representative oral formulations.

The bisulfate salt, and formulations thereof, are used as described in WO 97/40029 for the treatment of diseases caused by viruses, especially retroviruses such as the HIV virus.

DESCRIPTION OF SPECIFIC EMBODIMENTS

Example 1

Preparation of Bisulfate Salt from Ethanol

To a 500 mL three-necked round bottomed flask equipped with an overhead stirrer and dropping funnel, 15.013 g (0.0213 mole) of free base compound I and 113 mL of 200 proof ethanol were added with stirring. To this suspension, 1.28 mL concentrated sulfuric acid was added dropwise over 90 seconds. After the addition of sulfuric acid, a clear amber-colored solution was obtained. The solution was polish filtered using #1 Whatman filter paper and washed with 5 mL of 200 proof ethanol. To this solution was added 58 mL of heptane and 37.5 mg (0.25 wt %) of seed crystals of the compound of formula II followed by 55 mL of additional heptane. The resulting mixture was stirred for 6 hours at 300 rpm. The resulting crystal slurry was filtered and washed with 50 mL ethanol/heptane (1:1) solution and dried under vacuum at 60° C. overnight to afford 15.11 g of the desired crystalline bisulfate salt (88.4 mole % yield) having formula II above.

Characterizing Properties of Bisulfate Salt

Anal. Calcd. for $C_{38}H_{52}N_6O.1.0\ H_2SO_4$: C, 56.84; H, 6.78; N, 10.37; S, 3.99. Found: C, 56.72; H, 6.65; N, 10.41; S, 3.83. m.p. 195.0°, $H_2O$=0.28% (KF).

Example 2

Preparation of Bisulfate Salt from Acetone

5M $H_2SO_4$ (8.52 mL, 42.6 mM) was added dropwise to a suspension of the free base compound of formula I (30.0 g., 42.6 mM) in acetone (213 mL) stirred mechanically in a 50° C. oil-bath. A clear solution was obtained almost immediately. The solution was seeded with crystals of the free base compound of formula II. After two minutes, a precipitate formed which became a paste. The mixture was stirred at 50° C. for one hour, at 25° C. for 30 minutes and at 0° C. for 2 hours. The solid was filtered and the first filtrate was used to transfer the remaining material in the flask to the filtration funnel. The product was washed with acetone, then heptane, and dried under vacuum overnight to give 31.48 g (corrected yield 92%) of the bisulfate salt of formula II, m.p. 198–199° C. dec.

Anal. Calcd. $C_{38}H_{52}N_6O_7.1.0\ H_2SO_4.0.2\ H_2O$: C, 56.59; H, 6.80; N, 10.42; S, 3.98; $H_2O$, 0.45. Found: C, 56.66; H, 6.78; N, 10.50; S, 4.20; $H_2O$, 0.45 (KF).

Example 3

Preparation of Bisulfate Salt from Isopropanol

Aqueous sulfuric acid (5.0 M, 0.20 mL, 1 mM) was added to a suspension of the free base compound of formula I (0.704 g, 1.00 mM) in isopropanol (4.0 mL) chilled in an ice-bath. The ice-bath was removed and the mixture stirred at room temperature. The suspension had dissolved after 15 minutes. The solution was seeded with crystals prepared as in Examples 1 or 2 above and stirred for 5 hours. The solid was filtered and the filtrate was used to transfer the solid from the flask to the funnel. The product was washed with heptane and dried under vacuum to give 0.752 g of crystalline bisulfate salt of formula II, yield 90%, m.p. 160–190° C., dec.

Anal. Calcd. for $C_{38}H_{52}N_6O_7.1.0\ H_2SO_4.2.0\ H_2O$; C, 54.40; H, 6.97; N, 10.02; S, 3.82; $H_2O$, 4.29. Found: C, 54.25; H, 6.73; N, 10.02; S, 3.67; $H_2O$, 4.53 (KF).

The crystals obtained from isopropanol showed a powder x-ray diffraction pattern different from the crystals obtained from acetonitrile, ethanol-heptane or acetone. They are now referred to as Type-II crystals. The Type-I crystals appear to be an anhydrous/desolvated crystalline material while the Type-II crystals are a hydrated, hygroscopic crystalline form.

Example 4

Preparation of Capsule Formulations of Bisulfate Salt

A. Capsules (50 and 200 mg free base equivalent)

Capsules are provided for oral administration in which the capsule is a size #0, gray, opaque, hard gelatin capsule containing the bisulfate salt of formula II formulated as a wet granulation with lactose, crospovidone and magnesium stearate.

B. Capsules (100 mg free base equivalent)

Capsules are provided for oral administration in which the capsule is a size #0, gray, opaque, hard gelatin capsule containing the bisulfate salt of formula II suspended in Gelucire 44/14. Gelucire 44/14 is a saturated polyglycolized glyceride consisting of mono-, di- and triglycerides and mono- and di-fatty acid esters of polyethylene glycol. Capsules are prepared by melting Gelucire 44/14 at 45–70° C. followed by addition of the bisulfate salt with stirring. The molten mixture is filled into hard gelatin capsules and allowed to cool and solidify.

We claim:

1. The bisulfate salt having the formula

II

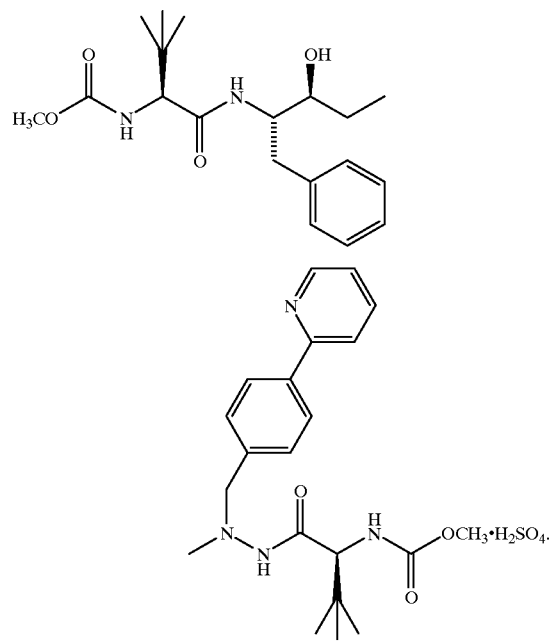

2. A pharmaceutical dosage form comprising the bisulfate salt of claim 1 and a pharmaceutically acceptable carrier.

* * * * *